US012618035B2

(12) United States Patent
Spitz et al.

(10) Patent No.: US 12,618,035 B2
(45) Date of Patent: May 5, 2026

(54) MICROFLUIDIC DEVICE

(71) Applicant: Technische Universität Wien, Vienna (AT)

(72) Inventors: Sarah Spitz, Vienna (AT); Peter Ertl, Vienna (AT); Jens Schwamborn, Wincheringen (DE); Silvia Bolognin, Luxembourg (LU)

(73) Assignee: Technische Universität Wien, Vienna (AT)

( * ) Notice: Subject to any disclaimer, the term of this patent is extended or adjusted under 35 U.S.C. 154(b) by 733 days.

(21) Appl. No.: 17/922,586

(22) PCT Filed: May 5, 2021

(86) PCT No.: PCT/EP2021/061860
§ 371 (c)(1),
(2) Date: Oct. 31, 2022

(87) PCT Pub. No.: WO2021/224329
PCT Pub. Date: Nov. 11, 2021

(65) Prior Publication Data
US 2023/0167391 A1     Jun. 1, 2023

(30) Foreign Application Priority Data
May 8, 2020     (EP) ..................................... 20173702

(51) Int. Cl.
C12M 3/00 (2006.01)
C12M 3/06 (2006.01)
C12N 5/0793 (2010.01)
(52) U.S. Cl.
CPC ............ C12M 23/16 (2013.01); C12M 21/08 (2013.01); C12N 5/0619 (2013.01)

(58) Field of Classification Search
CPC ..... C12M 23/16; C12M 21/08; C12N 5/0619; G01N 33/5058; G01N 33/4833;
(Continued)

(56) References Cited

U.S. PATENT DOCUMENTS

2009/0175834 A1* 7/2009 Poole ................... C12N 5/0623
435/368
2011/0244567 A1* 10/2011 Jeon ...................... C12N 5/0691
435/395
(Continued)

FOREIGN PATENT DOCUMENTS

WO     2009/089189 A2     7/2009
WO     2017/035119 A1     3/2017

OTHER PUBLICATIONS

European Search Report received for EP Patent Application No. 20173702.0, mailed on Jun. 29, 2020, 8 pages.
(Continued)

*Primary Examiner* — Liban M Hassan
(74) *Attorney, Agent, or Firm* — Workman Nydegger

(57) ABSTRACT

The present invention relates to a microfluidic device (1) for cultivating cells, in particular for generating brain organoids, comprising at least two fluid channels (2) positioned essentially opposite to each other and a main chamber (3) located between the fluid channels (2), wherein the main chamber (3) comprises at least one preferably sealable access opening, and each of the at least two fluid channels (2) is fluidly connected to the main chamber (3) at at least one point of contact (4), wherein a slotted structure (5) is provided at each point of contact (4) separating the main chamber (3) from the respective fluid channel (2), wherein the slotted structure (5) is permeable to a liquid.

17 Claims, 2 Drawing Sheets

(58) Field of Classification Search
CPC ..... B01L 2200/0647; B01L 2200/0668; B01L
2300/0816; B01L 2300/0848; B01L
2300/0867; B01L 2300/0877; B01L
2300/0887; B01L 2300/12; B01L
2400/086; B01L 2400/088; B01L
3/502761
See application file for complete search history.

(56) References Cited

U.S. PATENT DOCUMENTS

| | | | |
|---|---|---|---|
| 2011/0256574 A1 | 10/2011 | Zhang et al. | |
| 2014/0057311 A1 | 2/2014 | Kamm et al. | |
| 2015/0377861 A1* | 12/2015 | Pant | C12M 23/34 |
| | | | 435/395 |
| 2018/0267014 A1* | 9/2018 | Perlson | C12M 1/42 |

OTHER PUBLICATIONS

International Preliminary Report on Patentability received for PCT Patent Application No. PCT/EP21/061860, mailed on Nov. 17, 2022, 10 pages.
International Search Report and Written Opinion received for PCT Patent Application No. PCT/EP21/061860, mailed on Jul. 13, 2021, 12 pages.
Mariana S. Vieira et al: "Neural stem cell differentiation into mature neurons: Mechanisms of regulation and biotechnological applications", Biotechnology Advances., vol. 36, No. 7, Aug. 3, 2018 (Aug. 3, 2018) , pp. 1946-1970, XP055705717.

* cited by examiner

MICROFLUIDIC DEVICE

TECHNICAL FIELD

The present invention relates to the field of microfluidic test devices.

BACKGROUND ART

With yet unknown aetiology Parkinson disease (PD) constitutes the second most common neurodegenerative disease worldwide. Characterized by a loss of opaminergic neurons within the substantia nigra of the human midbrain, Parkinson disease results in a variety of symptoms including rigidity, akinesia as well as tremor. In addition, the disease is linked to a broad spectrum of non-motor symptoms such as disorders of the mood, cognitive dysfunction and hallucinosis. While several aspects including genetic and environmental factors have been identified to play a role in Parkinson disease the underlying causes still remain unknown.

This can at least in part be explained by the inability of animal models to adequately mimic important aspects of the human brain including histomorphology, spatiotemporal self-organization and neurodevelopment as well as the multifactorial nature of PD, all of which have called for sophisticated in vitro models capable of emulating and thus studying the disease and testing potential drug candidates.

With the emergence of induced pluripotent stem cell (iPSC) technology, it has now become possible to generate complex biological structures in vitro, including that of the human brain and midbrain on a personalized level. While iPSC derived human midbrain organoids were shown to display spatial organizations including cell-cell interactions as well as characteristic functions such as neuronal activity that mimic that of the human brain, they still fail to take mechanical stresses such as fluid flow into account. Interstitial fluid flow not only plays an important role in the delivery of nutrients and removal of metabolic waste but it implicates non-synaptic cell-cell communication, ionic homeostasis, cell migration as well as immune function. Furthermore, it is involved in drug delivery, distribution and clearance and thus of considerable importance when employing hMOs in the context of drug screening applications.

The production of organoids, in particular of brain or midbrain organoids, in microwell and cell culture plate formats are well-established methods. However, the formation of with such methods displays reproducability issues and the organoids formed show typically unphysiologic necortic cores. Hence, conventional strategies in induced pluripotent stem cell technology (iPSC) organoid technology are based on microwell and cell culture plate formats, lacking active nutrient and oxygen supply as well as the removal of degradation products at the same time resulting in inferior physiologic properties.

WO 2017/035119 A1 discloses a microfluidic system for modelling the blood brain barrier.

US 2014/0057311 A1 discloses a microfluidic device comprising one or more fluid channels and respective fluid channel inlets and fluid channel outlets.

US 2011/0256574 A1 discloses a microfluidic continuous flow device with different compartments.

WO 2009/089189 A2 discloses a microfluidic cell culture system with a medium inlet reservoir fluidically connected to a plurality of microfluidic medium channels.

MARIANA S. VIEIRA ET AL: "Neural stem cell differentiation into mature neurons: Mechanisms of regulation and biotechnological applications", BIOTECHNOLOGY ADVANVCES., vol. 36, no. 7, 1 Nov. 2018 (2018-11-01), pages 1946-1970, XP055705717, ISSN: 0734-9750 discloses biological background information about stem cell differentiation.

There is currently no in vitro system available which allows producing brain organoids to be used in tests which simulate an in vivo environment. Hence, it is an object of the present invention to provide method and means to overcome the drawbacks of current systems known in the art.

SUMMARY OF THE INVENTION

In order to overcome the drawbacks of the methods and devices known in the art for producing organoids, in particular brain organoids, the present invention provides a microfluidic device for cultivating cells, in particular for generating brain organoids, comprising at least two fluid channels positioned essentially opposite to each other and a main chamber located between the fluid channels, wherein the main chamber comprises at least one preferably sealable access opening, and each of the at least two fluid channels is fluidly connected to the main chamber at at least one point of contact, wherein a slotted structure is provided at each point of contact separating the main chamber from the respective fluid channel, wherein the slotted structure is permeable to a liquid. The main chamber comprises an inner top surface, an inner bottom surface situated opposite to the inner top surface, and an array of pillars extending from the inner top surface into the cross section of the main chamber in direction of the inner bottom surface.

It turned surprisingly out that the microfluidic device of the present invention allows longterm cultivation of mammalian cells to produce organoids. In particularly iPSC derived human midbrain organoids and any other organoid model under an interstitial flow regime can be produced using the device of the present invention.

The microfluidic device of the present invention particularly allows to elicit midbrain associated phenotypes, such as the expression of neuronal and dopaminergic neuron markers, shifts toward more physiologic metabolic profiles, the reduction of necrotic cores as well as the expression of neuromelanin and allows for fluid directed neurite outgrowth.

Another aspect of the present invention relates to an in vitro method for generating a brain organoid from pluripotent stem cells or neural progenitor cells in a microfluidic device according to the present invention and for testing the influence of a substance on said cerebral organoid comprising the steps of:

a) differentiating pluripotent stem cells or neural progenitor cells into mature neuronal cells, b) applying the mature neuronal cells of step a) to a main chamber of said microfluidic device, c) incubating the mature neuronal cells for at least 24 h and applying a medium fluid through at least one fluid channel of said microfluidic device to generate the cerebral organoid.

Reproducibly engineering and differentiating brain organoids, in particular human midbrain organoids (hMOs), under a biomimetic environment favorable for brain development is challenging. However, the microfluidic device of the present invention allows differentiating iPSC derived hMOs under dynamic conditions by directing interstitial fluid flow, preferably via hydrostatic pressure, through the growing organoid. The experimental data provided herein show that dynamic cultivation of iPSC derived hMOs maintains high cellular viabilities over prolonged cultivation periods of up 50 days and more and elicits midbrain associated phenotypes, as characterized by tyrosine hydroxylase positive dopaminergic neurons and neuromelanin formation, metabolic shifts and fluid directed neurite outgrowth.

Such microfluidic approaches provide an economically efficient platform for drug screening applications, requiring less medium and providing higher reproducability. Furthermore, neurite outgrowth will enable the development of models of higher complexity. The model allows not only to generate more physiologically relevant models, relevant for drug screening applications but in addition elicits postnatal phenoytypes early on, reducing time between development and screening of potential drug candidates. In addition, conventional methods retrieve age related phenomena (such as neuromelanin) very late on, important for studying and screening drugs in age related phenomena such as Parkinson.

DESCRIPTION OF EMBODIMENTS

Figure 1A:
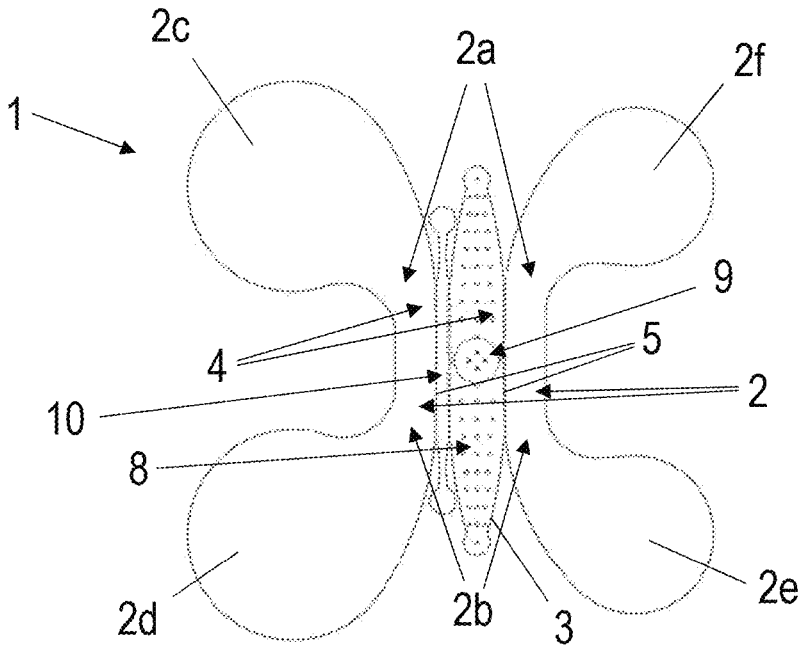
FIG. 1*a* shows a top view of a microfluidic device for cultivating cells according to the inventon.

The microfluidic device of the present invention comprises a main chamber located between at least two fluid channels. In said main channel mammalian cells may be positioned and cultivated whereby the at least two fluid channels can be used to supply the main channel with a culture medium via a slotted structure at the contact points of the main channel with the at least two fluid channels.

The slotted structure located between the main chamber and the fluid channels allows a regular controlled flow of fluid from said channels to and through the said chamber. Cells, cell aggregates and organoids positioned in the main chamber are consequently supplied with a fluid flow (e.g. cultivation medium) under constant conditions.

According to the present invention the main chamber comprises an inner top surface, an inner bottom surface situated opposite to the inner top surface, and an array of pillars extending from the inner top surface into the cross section of the main chamber in direction of the inner bottom surface.

The main chamber comprises an array of pillars. These pillars may serve to separate the fluid (e.g. medium) present in the at least two side channels and the hydrogel and the cells present in the main chamber to avoid that the hydrogel and the cells will flow into the side channels. However, the pillars are separated apart in order to allow that the fluid can pass in between the pillars from the side channels to the main chamber and vice versa. Furthermore, the presence of pillars is advantageous because it supports the outgrowth of the organoid formed inside the main chamber.

Preferably, the the array of pillars extending from the inner top surface into the cross section of the main chamber in direction of the inner bottom surface comprises at least some pillars connecting the innter top surface and the inner bottom surface.This configuarion allows for the measurement of neuronal activity directly in an organoid cultivated with the microfluidic device according to the invention. Preferably, these pillars connecting the innter top surface and the inner bottom surface are also covered with conductive material.

According to another preferred embodiment of the present invention the contact points are formed by elongated contact areas located on opposite sides of the main chamber.

The at least one contact point connecting the main chamber and the at least two side channels may have the form of an elongated contact area. Such a setup allows to create a constant fluid flow from the side channels into the main channel over a longer distance.

According to a further embodiment of the present invention the distance between the elongated contact areas is smaller than a length of the main chamber of the microfluidic device.

According to another preferred embodiment of the present invention the pillars are substantially perpendicular to the inner top surface.

The substantially perpendicular position of the pillars in the main channel is particularly advantageous to keep the hydrogel most efficiently within the main chamber.

According to a preferred embodiment of the present invention the array of pillars comprises from 1 to 50, preferably 2 to 40, more preferably 3 to 30, more preferably 5 to 25 pillars per mm$^2$.

The pillars of the main chamber have preferably a height from 100 to 5,000 µm, more preferably from 200 to 4,000 µm, more preferably from 300 to 3,000 µm, more preferably from 500 to 2,000 µm, and/or a diameter from 10 to 500 µm, preferably 20 to 400 µm, more preferably 50 to 300 µm, more preferably 100 to 300 µm.

According to a further preferred embodiment of the present invention the inner bottom surface of the main chamber comprises at least one recess.

One or more cell aggregates or organoids may be stably positioned in the at least one recess of the main chamber. The at least one recess on the bottom of the main chamber is useful to stabilize cell aggregates or organoids within the main chamber.

According to a preferred embodiment of the present invention the at least one recess has a substantial cylindrical or substantial hemispherical shape.

It turned out that cell aggregates and organoids can be formed in recesses of substantial cylindrical or hemispherical shape.

According to another preferred embodiment of the present invention the at least two fluid channels are fluidly connected to a fluid channel inlet and a fluid channel outlet.

In order to produce a fluid flow within the at least two fluid channels, these channels are fluidly connected to an inlet and to an outlet.

According to a further preferred embodiment of the present invention the fluid channel inlet and the fluid channel outlet are fluidly connected to a medium reservoir.

The cell aggregates and organoids within the main chamber have to be supplied with nutrients and thus with a culture medium. Said medium can be introduced into the main chamber by introducing it into the fluid channel using a medium reservoir. The medium reservoir has the advantage that it can be filled with sufficient medium required for the cultivation and/or the production of cell organoids.

The medium reservoir of the microfluidic device of the present invention may have any shape and may have a defined volume for taking up, for instance, sufficient medium to supply the main chamber of the device with medium at a certain level.

In order to establish a constant and continuous medium flow within the fluid channels and within the main chamber of the microfluidic device of the present invention it is advantageous that the medium reservoirs fluidly connected to said channels have varying volumes. Due to varying volumes of the medium reservoirs a hydrostatic pressure from the reservoir having a larger volume to the reservoir having a lower volume can be established. The resservoirs with the larger volume may be 2 to 20 times, preferably 2 to 15 times, more preferably 2 to 10 times, more preferably 2 to 8 times, more preferably 3 to 6 times, larger compared to those with the lower volume. The ratio of the volume of the reservoirs to volume of the main chamber may be within 50:1 to 2:1, preferably 40:1 to 3:1, more preferably 35:1 to 4:1, more preferably 30:1 to 5:1.

According to a preferred embodiment of the present invention the medium reservoir(s) fluidly connected to the fluid channel inlet(s) may have a larger volume than the medium reservoir(s) fluidly connected to the fluid channel outlet(s).

In such a configuration the flow of the medium is directed through the fluid channels from the fluid channel inlet to the fluid channel outlet. By passing through the fluid channel medium is supplied to the main chamber via the slotted structure provided at each point of contact between the fluid channels and the main chamber.

Alternatively, the medium reservoir(s) fluidly connected to the fluid channel inlet(s) may have a smaller volume than the medium reservoirs fluidly connected to the fluid channel outlet(s).

In such a configuration, the consumption of media contained in the medium reservoir(s) is reduced.

In order to direct a much higher and constant flow rate through the main chamber of the microfluidic device of the present invention, the medium reservoirs fluidly connected to one fluid channel have a larger volume than the medium reservoirs fluidly connected to another fluid channel at the opposed side of the main chamber. Such a configuration is advantageous because it allows to bring medium to the cells within the main chamber more constantly over the whole contact area (channel/chamber) comprising the slotted structure.

According to a preferred embodiment of the present invention the main chamber comprises a fluid main chamber inlet and a fluid main chamber outlet.

In order to bring cells, hydrogel and other particles and substances into the main chamber of the microfluidic device of the present invention the main chamber may adavantageously comprise one or more fluid main chamber inlets and one or more fluid main chamber outlets.

According to another preferred embodiment of the present invention the slotted structure comprises an electrically conductive material to form an electrode.

The slotted structure at the contact areas between the fluid channels and the main chamber may comprise on their surface or may be made at least partially of an electrically conductive material (e.g. metal, electrically conductive polymer). The slotted structure having a contact area to a first fluid channel may serve as anode whereas the slotted structure opposed thereto may serve as cathode. Electrically conductive slotted structures are particularly advantageous because they allow to either stimulate electrically the organoid within the main chamber or to perform measurements like those typically performed with microelectrode arrays (e.g. extracellular field potential measurements, electro-physiologic activity measurements, elektrophysiologic activity, neuronal synchrony measurements).

According to a preferred embodiment of the present invention the slots of the slotted structure are spaced apart from each other by at least 50 μm, preferably by at least 80 μm, more preferably by at least 100 μm, more preferably by at least 120 μm.

It turned out that it is particularly adavantageous that the slots of the slotted structure are spaced apart at least for 50 μm. This allows a sufficient flow rate through the main chamber. Furthermore, due to their size cell aggregates and organoids present in the main chamber can not be washed out if the slots of the slotted structure are spaced apart as defined herein.

According to a further preferred embodiment of the present invention the slots of the slotted structure are spaced apart from each other by a maximum of 800 μm, preferably 600 μm, more preferably 500 μm.

According to another preferred embodiment of the present invention an inner surface of the main chamber, an inner surface of the at least two fluid channels, and/or the slotted structure is covered by an antifouling layer.

In order to avoid the formation of biofilms within the microfluidic device of the present invention those parts of the device having contact with the cells may be at least partially coated with an antifouling layer.

According to a further preferred embodiment of the present invention the antiflouing layer comprises or consists of a coating selected from the group consisting of an Slayer, phosphorylcholine, phospholipids, polyethylene glycol and/ or polythylene oxide based coatings, poly zwitterionic based coatings, saccharide based coatings, fluoro-based coatings, polyhydroxy based coatings and combinations thereof.

The array of pillars extending from the inner top surface into the cross section of the main chamber in direction of the inner bottom surface of the microfluidic device according to the invention may comprise at least some pillars connecting the innter top surface and the inner bottom surface.

This configuarion allows for the measurement of neuronal activity directly in an organoid cultivated with the micro-fluidic device according to the invention. Preferably, these pillars connecting the innter top surface and the inner bottom surface are also covered with conductive material.

Figure 1B:
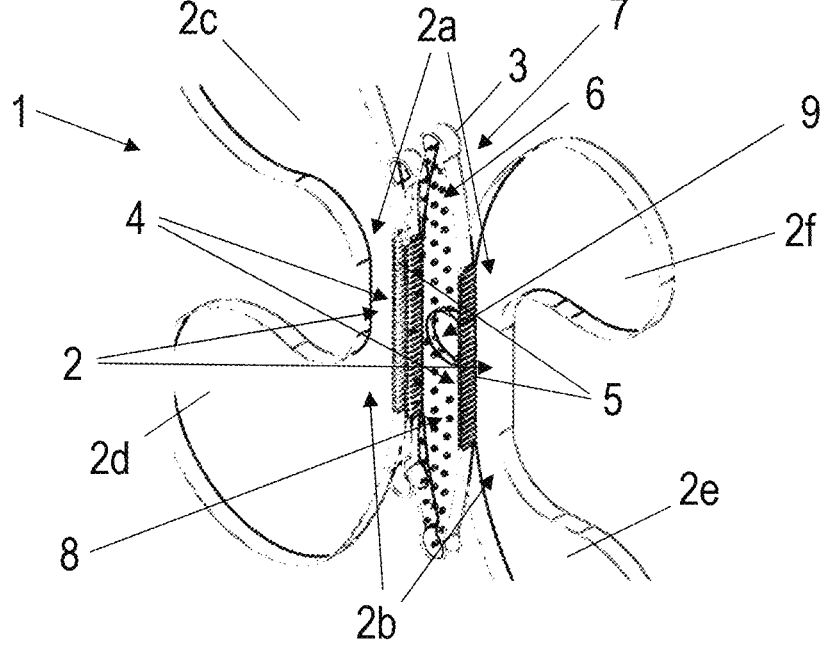
FIG. 1*b* shows the microfluidic device according to FIG. 1*a* in a perspective view.

FIG. 1a and FIG. 1b show a microfluidic device 1 for cultivating cells according to the invention, wherein FIG. 1a is a top view, and FIG. 1b is a perspective view of the microfluidic device 1. The microfluidic device 1 according to the invention comprises at least two fluid channels 2 positioned essentially opposite to each other, and a main chamber 3 located between the fluid channels 2. According to a preferred embodiment of the microfluidic device 1, the microfluidic device 1 comprises two fluid channels 2, as depicted in FIG. 1a and FIG. 1b. The main chamber 3 comprises at least one preferably sealable access opening, for introducing for example cell infused hydrogel into the main chamber. Each of the at least two fluid channels 2 is fluidly connected to the main chamber 3 at least one point of contact 4. At each point of contact 4, a slotted structure 5 is provided separating the main chamber 3 from the respective fluid channel 2, wherein the slotted structure 5 is permeable to a liquid or liquids in general. According to the preferred embodiment of the invention, the slotted structure 5 comprises of a series of slits, oriented preferably in parallel to each other at each point of contact 4 between the main chamber 3 and one of the fluid channels 2. In order to cultivate cells with the microfluidic device 1 according to the invention, for example a hydrogel infused with cells is introduced into the main chamber 3 via the access opening. Furthermore, a constant flow of nutrient liquid is provided via the fluid channels 2.

As shown in FIG. 1a and FIG. 1b, the main chamber 3 preferably comprises an inner top surface 6, an inner bottom surface 7 situated opposite to the inner top surface 6, and an array of pillars 8 extending from the inner top surface 6 into the cross section of the main chamber 3 in direction of the inner bottom surface 7. The inner top surface 6 is shown in FIG. 1a and FIG. 1b in a transparent way in order to reveal the pillars. The array of pillars 8 provides a support structure for an organoid growing in the main chamber 3, preventing the organoid from being displaced during the growth process. The pillars are preferably oriented substantially perpendicular to the inner top surface 6. Furthermore, according to a preferred embodiment, the array of pillars 8 comprises from 1 to 50, preferably 2 to 40, more preferably 3 to 30, more preferably 5 to 25 pillars per mm². Additionally, the pillars have a height from 100 to 5,000 μm, preferably 200 to 4,000 μm, more preferably 300 to 3,000 μm, more preferably 500 to 2,000 μm, and a diameter from 10 to 500 μm, preferably 20 to 400 μm, more preferably 50 to 300 μm, more preferably 100 to 300 μm.

The array of pillars 8 extending from the inner top surface 6 into the cross section of the main chamber 3 in direction of the inner bottom surface 7 of the microfluidic device 1 according to the invention may comprise at least some pillars connecting the innter top surface 6 and the inner bottom surface 7.

This configuarion allows for the measurement of neuronal activity directly in an organoid cultivated with the microfluidic device 1 according to the invention. Preferably, these pillars connecting the innter top surface 6 and the inner bottom surface 7 are also covered with conductive material.

According to the preferred embodiment of the invention, the contact points 4 are formed by elongated contact areas, located on opposite sides of the main chamber 3. This arrangement offers the advantage of an increased fluid exchange between the fluid channels 2 and the main chamber 3. Furthermore, due to the increased cross section of the contact areas, elongated organoids can be produced and sustained within the main chamber 3.

Preferably, a distance between the elongated contact areas is smaller than a length of the main chamber 3 of the microfluidic device 1. This setup further supports the growth of elongated organoids.

As shown in FIGS. 1a and 1b, the preferred embodiment of the microfluidic device 1 according to the invention comprises at least one recess 9 in the inner bottom surface 7 of the main chamber. The at least one recess 9 serves as an anchoring point for the organoid, and preferably has a substantial cylindrical or substantial hemispherical shape.

Accordoing to the preferred embodiment, each of the at least two fluid channels 2 is fluidly connected to a respective fluid channel inlet 2a and a respective fluid channel outlet 2b. The fluid channel inlet 2a and the fluid channel outlet 2b are fluidly connected to a medium reservoir 2c, 2d, 2e, 2f.

Furthermore, the slotted structure 5 preferably comprises an electrically conductive material to form an electrode.

An inner surface of the main chamber, an inner surface of the at least two fluid channels 2, and/or the slotted structure 5 is preferably covered by an anti fouling layer, which preferably comprises or consists of a coating selected from the group consisting of an S-layer, phosphorylcholine, phospholipids, polyethylene glycol and/or polythylene oxide based coatings, poly zwitterionic based coatings, saccharide based coatings, fluoro-based coatings, polyhydroxy based coatings and combinations thereof.

The main chamber 3 of the microfluidic device 1 according to the invention comprises in the preferred embodiment shown in the figures a flow regulation chamber 10, which is situated next to the contact point 4 bewtween the main chamber 3 and one of the fluid channels 2. The flow regulation chamber 10 provides an additional flow resistance between the fluid channel 2 and the main chamber 3.

Another aspect of the present invention relates to an in vitro method for generating a brain organoid from pluripotent stem cells or neural progenitor cells in a microfluidic device according to the present invention and for testing the influence of a substance on said brain organoid comprising the steps of:

a) differentiating pluripotent stem cells or neural progenitor cells into mature neuronal cells, b) applying the mature neuronal cells of step a) to a main chamber of said microfluidic device, c) incubating the mature neuronal cells for at least 24 h and applying a medium fluid through at least one fluid channel of said microfluidic device to generate the cerebral organoid.

The microfluidic device can be used for generating a brain organoid from pluripotent stem cells or neural progenitor cells. The design of the microfluidic device of the present invention allows to generate brain organoids in a short period of time under natural conditions. The slotted structure between the fluid channels and the main chambers allows to get conditions where the growing organoid is sufficiently supplemented with (fresh) medium under constant conditions.

In a first step pluripotent stem cells or neural progenitor cells are differentiated into mature neuronal cells. This step can be done outside the microfluidic device of the present invention. However, in a particularly preferred embodiment of the present invention this initial step can also occur in the main chamber of the device. In such a case the pluripotent stem cells or neural progenitor cells are directly applied to the main chamber of the microfluidic device and differentiated into mature neuronal cells directly therein.

Methods for differentiating pluripotent stem cells or neural progenitor cells into mature neuronal cells are well known in the art (see e.g. N Gunhanlar et al. (Mol Psychiatry 23 (2018): 1336-1344); Schulz T C et al. (Stem Cells 22 (2004): 1218-1238); Kriks S et al. (Nature 480 (2011): 547-551)).

In a second step of the method of the present invention the mature neuronal cells of step a) are applied to the main chamber of the microfluidic device of the present invention via a fluid main chamber inlet.

The formation of the brain organoid occurs in a third step where the mature neuronal cells are incubated for at least 24 h, preferably for at least 48 h, more preferably for at least 72 h, by applying a medium fluid through at least one fluid channel of the microfluidic device. In an alternative embodiment of the present invention the medium can also be applied to the main chamber via a fluid main chamber inlet and removed from said main chamber by a fluid main chamber outlet.

According to a preferred embodiment of the present invention the fluid flow is directed in a step d) trough the brain organoid for at least 12 h, preferably at least 24 h, more preferably at least 36 h, more preferably at least 48 h, to induce brain maturation.

In order to produce an aged or matured brain organoid a fluid flow from the fluid channels to and/or through the main chamber is applied for a certain period of time. In the course of this additional step a medium is applied which is disclosed in WO 2017/060884.

According to another preferred embodiment of the present invention the mature neuronal cells of step a) are applied to the microfluidic device together with a hydrogel or subsequently to the application of a hydrogel to the microfluidic device. The hydrogel has a Young's Modulus of less than 1.5 kPa, preferably less than 1 kPa.

In order to produce a brain organoid within the microfluidic device of the present invention it is particularly preferred to apply also a hydrogel to the main chamber of the device. The hydrogel forms a matrix for the organoid to be produced.

According to a further preferred embodiment of the present invention 1 to 50 mg/ml, preferably 2 to 40 mg/ml, more preferably 3 to 35 mg/ml, more preferably 4 to 30 mg/ml, hydrogel is applied to the microfluidic device According to another preferred embodiment of the present invention the hydrogel is selected from the group consisting of Matrigel, Geltrex, fibrin, human platelet lysate based matrix, ECM based surrougates and dextran.

According to a preferred embodiment of the present invention 1 to 50 mg/ml, preferably 2 to 40 mg/ml, more preferably 3 to 35 mg/ml, more preferably 4 to 30 mg/ml, more preferably 5 to 22 mg/ml, Matrigel is applied to the microfluidic device.

According to a further preferred embodiment of the present invention 1 to 50 mg/ml, preferably 2 to 40 mg/ml, more preferably 3 to 35 mg/ml, more preferably 4 to 30 mg/ml, more preferably 5 to 22 mg/ml, Geltrex is applied to the microfluidic device.

According to a preferred embodiment of the present invention the pluripotent stem cells or neural progenitor cells are neuroepithelial stem cells, preferably multipotent neuroepithelial stem cells.

These cells can be differentiated into mature neuronal cells using standard protocols (see e.g. N Gunhanlar et al. (Mol Psychiatry 23 (2018): 1336-1344); Schulz T C et al. (Stem Cells 22 (2004): 1218-1238); Kriks S et al. (Nature 480 (2011): 547-551); Reinhardt P et al. (PLOS One. 8 (2013): e59252); Qing X et al. (Stem Cell Res. 24 (2017): 44-50)).

According to another preferred embodiment of the present invention in step c) the medium fluid is applied with an average flow rate of 0.001 to 5 µl/min, preferably 0.001 to 4 µl/min, more preferably 0.001 to 3 µl/min, more preferably 0.001 to 2 µl/min.

According to a further preferred embodiment of the present invention in step c) the medium fluid is applied with a flow rate of 0.001 µm/s to 5 µm/s, preferably 0.01 to 4 µm/s, more preferably 0.02 to 2 µm/s, for up to 36 h, preferably up to 30 h, more preferably up to 24 h, more preferably up to 20 h, followed by a static phase where the flow rate of the medium fluid is less than 0.1 µm/s, preferably less than 0.05 µm/s, more preferably less than 0.02 µm/s, for up to 48 h, preferably up to 36 h, more preferably up to 24 h, more preferably up to 12 h.

According to a preferred embodiment of the present invention after step c) a substance is added to at least one fluid channel to test the influence of a substance on said cerebral organoid.

The microfluidic device of the present invention comprising an organoid, preferably a brain, more preferably a midbrain organoid, can be used for different purposes. One major use is to test the influence of substances on the organoid. This allows to identify new substances which may be used in the treatment or prevention of diseases. Hence, it is particularly preferred to add substances to a medium fluid applied to the device of the present invention. However, the organoid may not only exposed to specific substances but also to physical changes like temperature, to radiation (e.g. gamma radiation, UV radiation), to changes of the osmolarity of the medium. All possible influences on the organoid can be monitored using the device of the present invention.

According to another preferred embodiment of the present invention an electrophysiological activty, a metabolic activity, a neurotransmitter concentration, a physiologic phenotype, a disease phenotype or a protein aggregation is determined.

The present invention is further defined by the following embodiments and examples, however, without being restricted thereto.

EMBODIMENTS

1. A microfluidic device (1) for cultivating cells, in particular for generating brain organoids, comprising at least two fluid channels (2) positioned essentially opposite to each other and a main chamber (3) located between the fluid channels (2), wherein the main chamber (3) comprises at least one preferably sealable access opening, and each of the at least two fluid channels (2) is fluidly connected to the main chamber (3) at at least one point of contact (4), wherein a slotted structure (5) is provided at each point of contact (4) separating the main chamber (3) from the respective fluid channel (2), wherein the slotted structure (5) is permeable to a liquid.

2. Microfluidic device (1) according to embodiment 1, wherein the main chamber (3) comprises an inner top surface (6), an inner bottom surface (7) situated opposite to the inner top surface (6), and an array of pillars (8) extending from the inner top surface (6) into the cross section of the main chamber (3) in direction of the inner bottom surface (7).

3. Microfluidic device (1) according to embodiment 2, wherein the contact points (4) are formed by elongated contact areas located on opposite sides of the main chamber (3).

4. Microfluidic device (1) according to embodiment 3, wherein the distance between the elongated contact areas is smaller than a length of the main chamber (3) of the microfluidic device (1).

5. Microdfluidic device (1) according to any one of embodiments 2 to 4, wherein the pillars are substantially perpendicular to the inner top surface (6).

6. Microdfluidic device (1) according to any of embodiments 2 to 5, wherein the array of pillars (8) comprises 1 to 50, preferably 2 to 40, more preferably 3 to 30, more preferably 5 to 25 pillars per $mm^2$.

7. Microdfluidic device (1) according to any one of embodiments 2 to 6, wherein the pillars have a height from 100 to 5,000 µm, preferably from 200 to 4,000 µm, more preferably from 300 to 3,000 µm, more preferably from 500 to 2,000 µm, and a diameter from 10 to 500 µm, preferably from 20 to 400 µm, more preferably from 50 to 300 µm, more preferably from 100 to 300 µm.

8. Microdfluidic device (1) according to any one of embodiments 2 to 7, wherein the inner bottom surface (7) of the main chamber (3) comprises at least one recess (9).

9. Microfluidic device (1) according to embodiment 8, wherein the at least one recess (9) has a substantial cylindrical or substantial hemispherical shape.

10. Microdfluidic device (1) according to any one of embodiments 1 to 9, wherein each of the at least two fluid channels (2) is fluidly connected to a respective fluid channel inlet (2a) and a respective fluid channel outlet (2b).

11. Microfluidic device (1) according to embodiment 10, wherein the fluid channel inlet (2a) and the fluid channel outlet (2b) are fluidly connected to medium reservoirs (2c, 2d, 2e, 2f).

12. Microfluidic device (1) according to embodiment 11, wherein the medium reservoirs (2c, 2d, 2e, 2f) have varying volumes.

13. Microfluidic device (1) according to embodiment 11, wherein the medium reservoirs (2c, 2f) fluidly connected to the fluid channel inlet (2a) have a larger volume than the medium reservoirs (2d, 2e) fluidly connected to the fluid channel outlet (2b).

14. Microfludic device (1) according to embodiment 11, wherein the medium reservoirs (2c, 2f) fluidly connected to the fluid channel inlet (2a) have a smaller volume than the medium reservoirs (2d, 2e) fluidly connected to the fluid channel outlet (2b).

15. Microfluidic device (1) according to embodiment 11 or 12, wherein the medium reservoirs (2c, 2f) fluidly connected to one fluid channel (2) have a larger volume than the medium reservoirs (2d, 2e) fluidly connected to another fluid channel (2).

16. Microfluidic device (1) according to any one of embodiments 1 to 15, wherein the main chamber (3) comprises a fluid main chamber inlet and a fluid main chamber outlet.

17. Microfluidic device (1) according to any one of embodiments 1 to 12, wherein the slotted structure (5) comprises an electrically conductive material to form an electrode.

18. Microfluidic device (1) according to any one of embodiments 1 to 17, wherein the slots of the slotted structure (5) are spaced apart from each other by at least 50 μm, preferably by at least 80 μm, more preferably by at least 100 μm, more preferably by at least 120 μm.

19. Microfluidic device (1) according to any one of embodiments 1 to 18, wherein an inner surface of the main chamber, an inner surface of the at least two fluid channels (2), and/or the slotted structure (5) is covered by an antifouling layer.

20. Microfluidic device (1) according to embodiment 19, wherein the antiflouing layer comprises or consists of a coating selected from the group consisting of S-layer, phosphorylcholine, phospholipids, polyethylene glycol and/or polythylene oxide based coatings, poly zwitterionic based coatings, saccharide based coatings, fluoro-based coatings, polyhydroxy based coatings and combinations thereof.

21. Microfluidic device (1) according to any one of embodiments 1 to 20, wherein the array of pillars (8) extending from the inner top surface (6) into the cross section of the main chamber (3) in direction of the inner bottom surface (7) comprises at least some pillars connecting the innter top surface (6) and the inner bottom surface (7).

22. An in vitro method for generating a brain organoid from pluripotent stem cells or neural progenitor cells in a microfluidic device according to any one of embodiments 1 to 21 and for testing the influence of a substance on said brain organoid comprising the steps of:

a) differentiating pluripotent stem cells or neural progenitor cells into mature neuronal cells, b) applying the mature neuronal cells of step a) to a main chamber of said microfluidic device, c) incubating the mature neuronal cells for at least 24 h and applying a medium fluid through at least one fluid channel of said microfluidic device to generate the brain organoid.

23. Method according to embodiment 22, wherein in a step d) the fluid flow is directed trough the brain organoid for at least 12 h, preferably at least 24 h, more preferably at least 36 h, more preferably at least 48 h, to induce brain maturation.

24. Method according to embodiment 22 or 23, wherein the mature neuronal cells of step a) are applied to the microfluidic device together with a hydrogel or subsequently to the application of a hydrogel to the microfluidic device.

25. Method according to embodiment 24, wherein 1 to 50 mg/ml, preferably 2 to 40 mg/ml, more preferably 3 to 35 mg/ml, more preferably 4 to 30 mg/ml, hydrogel is applied to the microfluidic device 26. Method according to embodiment 24 or 25, wherein the hydrogel is selected from the group consisting of Matrigel, Geltrex, fibrin, human platelet lysate based matrix, ECM based surrougates and dextran.

27. Method according to embodiment 26, wherein 1 to 50 mg/ml, preferably 2 to 40 mg/ml, more preferably 3 to 35 mg/ml, more preferably 4 to 30 mg/ml, more preferably 5 to 22 mg/ml, Matrigel is applied to the microfluidic device.

28. Method according to embodiment 26, wherein 1 to 50 mg/ml, preferably 2 to 40 mg/ml, more preferably 3 to 35 mg/ml, more preferably 4 to 30 mg/ml, more preferably 5 to 22 mg/ml, Geltrex is applied to the microfluidic device.

29. Method according to any one of embodiments 22 to 28, wherein the pluripotent stem cells or neural progenitor cells are neuroepithelial stem cells, preferably multipotent neuroepithelial stem cells.

30. Method according to any one of embodiments 22 to 29, wherein in step c) the medium fluid is applied with an average flow rate of 0.001 to 5 μl/min, preferably 0.001 to 4 μl/min, more preferably 0.001 to 3 μl/min, more preferably 0.001 to 2 μl/min.

31. Method according to any one of embodiments 22 to 30, wherein in step c) the medium fluid is applied with a flow rate of 0.001 μm/s to 5 μm/s, preferably 0.01 to 4 μm/s, more preferably 0.02 to 2 μm/s, for up to 36 h, preferably up to 30 h, more preferably up to 24 h, more preferably up to 20 h, followed by a static phase where the flow rate of the medium fluid is less than 0.1 μm/s, preferably less than 0.05 μm/s, more preferably less than 0.02 μm/s, for up to 48 h, preferably up to 36 h, more preferably up to 24 h, more preferably up to 12 h.

32. Method according to any one of embodiments 22 to 31, wherein after step c) a substance is added to at least one fluid channel to test the influence of a substance on said cerebral organoid.

33. Method according to any one of embodiments 22 to 32, wherein anelectrophysiological activty, a metabolic activity, a neurotransmitter concentration or a protein aggregation is determined.

EXAMPLE

Material and Methods

Chip Fabrication

Microstructures were fabricated by soft lithography from a CNC milled mold using polydimethylsiloxane (PDMS, Sylgard® 184 Silicone Elastomer Kit, Down Corning). After polymerization at 80° C., molded PDMS was bonded to glass substrates using air plasma (Harrick Plasma, High Power, 2 min). Microfluidic devices equipped with oxygen sensors were generated by the deposition of microparticles into drilled cavities within glass substrates by the use of a pipette. After drying for 2 h at room temperature, the microparticles were immobilized to the glass substrate and the fluidic structures were sealed, employing air plasma. Prior to use microfluidic devices were sterilized employing 70% ethanol as well as UV plasma.

Finite Volume CFD Simulation

A multipurpose finite volume computational fluid dynamics (CFD) code (Ansys Fluent 6.3.26, www.ansys.com/ Open Foam www.openfoam.org) was used for solving the flow problem. The geometry consisting of the hydrogel cavity, the two feed channels as well as the two collection units was split into about 136000 hexahedral control volumes. The grid pillars at the gel inflow and outflow boundary have been fully resolved.

For adequate numerical accuracy, second or higher order discretization schemes have been selected for all flow variables (Navier-Stokes equation-momentum conservation, Continuity equation-mass conservation) and for the species equations, as previously reported X. All wall boundaries were treated as ideally smooth; no slip boundary conditions (zero flow velocity at the wall) were selected for all surfaces. The outlet was set to pressure outlet at a standard pressure of p=1 atm (101, 325 Pa). The hydrogel region was approximated as homogeneous and isotropic porous zone (Darcy-Forchheimer equation) with a constant porosity of $\varepsilon$=0.99, and a viscous resistance of R=1.33.1013 $1/m^2$ for all directions has been assumed.

Isothermal flow was assumed, no temperature or energy field was solved. For simplicity, Newtonian fluid behavior was applied for the simulation and runs with a constant dynamic viscosity and constant density (incompressible) for all of the mixture components. As the concentrations of the dissolved species in the fluid are low, the properties of the solvent, water, have been used for the simulation ($\rho$=993 $kg/m^3$, $\eta$=0.001003 Pa·s at 37° C.). The diffusion coefficients for the tracer components have been estimated according to literature values (glucose: 0.18 kDa-4.10-10 $m^2/s$, oxygen: 32 Da-2.10-9 $m^2/s$, water: 18 Da-2.10-9 $m^2/s$) assuming a dilute solution13. To investigate the cross mixing of the two inlet channel fluids, different water species have been used for both inlets. Simulations were carried out on the cluster server cae.zserv.tuwien.ac.at (operated by the IT department of TU Wien, www.zid.tuwien.ac.at).

As the major flow resistances are inside the hydrogel and in the flow channels, but not in the feed and collection cavities, a simplification was used: To reduce the computational effort, steady state simulations for different selected feed cavity filling levels have been carried out. The simulated filling level was translated into a corresponding relative pressure difference between feed inlet zone and pressure outlet.

Human Midbrain Organoids (hMO) Generation and On-Chip Cultivation

For the generation of hMOs 3,000 multipotent neuroepithelial stem cells (Stem Cell Reports 8 (2017): 1144-1154) were seeded into each well of an ultra-low attachment round bottom 96-well plate (Greiner). Seeded cells were kept under maintenance conditions (50:50 mixture of DMEM-F12 (Sigma Aldrich) and Neurobasal medium (Gibco) supplemented with 1:200 N2 supplement (Invitrogen), 1:100 B27 supplement lacking vitamin A (Invitrogen), 1% L-glutamine, 1% penicillin/streptomycin (Invitrogen), 3 µM CHIR-99021 (Axon Medchem), 0.5 µM SAG (Merck), 10 µM SB-431542 (Ascent Scientific), 250 nM LDN (Sigma), 5 µM ROCK-inhibitor (Sigma Aldrich) and 200 µM ascorbic acid (Sigma)) for 7 days. Subsequently pre-patterning was started by the withdrawal of LDN, Y and SB. After 3 days the concentration of CHIR was reduced to 0.7 µM. On day 9 of differentiation, the medium was changed to neuronal maturation medium including 10 UM DAPT, 500 µM db CAMP, 10 ng/mL hBDNF and hGDNF (Prepotech), 1 ng/ml TGF-β3 (Peprotech) as well as 2.5 ng/ml Activin A (Thermo Fisher Scientific). The organoids were kept under static culture conditions with media changes every other to third day for up to 70 days. Subsequently hMOs were fixed with 4% PFA at room temperature over night before being washed with PBS 3 times.

For on-chip hMO cultivation pre-differentiated organoids suspended in Matrigel® (Corning®) were transferred into the chip on day 0 of maturation phase. After 2 hours of stationary culture, hMOs were subjected to an alternating cultivation protocol consisting of 15 h dynamic cultivation followed by a 33 h static period for the entire cultivation span of up to 50 days. Dynamic cultivation was achieved by filling the feed medium reservoirs up to a 3 mm feeding level, while medium at the collector side was kept at 0.6 mm height. Medium was exchanged every 48 h.

On-Chip Oxygen Monitoring

On-chip oxygen monitoring was carried out at a sampling frequency of 1 Hz using a FireStingO2 optical oxygen meter (Pyroscience) connected to optical fibers (length 1 m, outer diameter 2.2 mm, fiber diameter 1 mm). Integrated sensors were calibrated using a $CO_2/O_2$ oxygen controller ($CO_2$—$O_2$-Controller 2000, Pecon GmbH) equipped with integrated zirconium oxide oxygen sensors. Oxygen measurements were performed once a week. For this purpose, chips were sealed with PCR foil and transferred into an external incubation chamber setup. Samples were measured for 10 minutes to guarantee proper equilibration. Oxygen demand was subsequently calculated according to the following formula: hMO oxygen demand ($\Delta PO2$)=PO2 blank–PO2 hMO.

Viability Assay and Morphological Characterization of hMOs

To monitor the viability of hMOs a viability assay employing calcein-AM and ethidium-H1 (Invitrogen, L3224) was performed every week. Images were analyzed using the ImageJ plugin Color Pixel Plugin. Cellular viabilities were determined by dividing the number of green pixels by the total number of red and green pixels, while exposure time and focus plane were kept constant for each analysis. To obtain information on both hMO growth as well as neurite outgrowth, organoid diameter (highest diameter of each organoid) and neurite lengths were assessed manually using ImageJ.

Fontana Masson Staining

Prior to Fontana Masson staining histological sections were deparaffinated and rehydrated. After 10 minutes of staining in Lugol's solution (potassium iodide, iodine (Roth)) sections were transferred into 5% sodium thiosulfate solution for 2 minutes (Morphisto). Subsequently slides were rinsed three times in distilled water. Thereafter slides were exposed to ammoniacal silver solution (ammonium hydroxide (Alfa Aesar), silver nitrate (Roth)) at 60° C. for two hours, before the slides were rinsed again in distilled water and exposed to 0.2% gold chloride solution for 3 minutes. Afterwards, slides were rinsed with distilled water, transferred again into a 5% sodium thiosulfate solution for two minutes and rinsed once more with tap water for two minutes. Cell nuclei were stained with 1% Nuclear fast red (Merck). Slides were dehydrated using ethanol before being mounted with Consul Mount (Thermo Fisher Scientific).

Immunofluorescence

For the immunofluorescence staining of cultured hMOs, fixed organoids were embedded in a 3% low-melting point agarose (Biozym) in PBS. Subsequently 50 μm thick sections were cut using a vibratome (Leica VT1000s) and centersections were used for assessing TH/FOXA2/TUJ1 expression. Prior to the immunostaining, sections were permeabilized using 0.5% Triton X-100 in PBS. Depending on the antibody, permeabilization times varied between 30 min and 2 h. Unspecific antigen blocking was achieved by incubating cut sections for 2 h in 2.5% donkey serum, 2.5% BSA, 0.1% Triton X-100 and 0.1% sodium azide, followed by primary antibody incubation at 4° C. for 48 h on a shaker. Antibodies were diluted in blocking buffer as follows: rabbit anti-TH (1:1000, Abcam), mouse anti-FOXA2 (1:250, Santa Cruz Biotechnology), chicken anti-TUJ1 (1:600 Millipore), goat anti-SOX2 (1:200, R&D Systems) and rabbit anti-CC3 (1:200, Cell Signalling). Afterwards sections were washed three times in PBS containing 0.01% Triton X-100 before being blocked for 30 min at room temperature on a shaker. This was followed by the incubation with secondary antibodies diluted in PBS containing 0.01% Triton X-100 and Hoechst-33342 nuclear dye (1:1000; Sigma-Aldrich). All secondary antibodies (Invitrogen) were conjugated to Alexa Fluor fluorochromes. Sections were mounted in Fluoromount-G mounting medium (Southern Biotech) and analysed employing a confocal laser scanning microscope (Zeiss LSM 710).

Results

Chip Design

To allow for the physiologic cultivation of hMOs on chip under an interstitial flow regime a hydrostatic pressure driven flow-based design was selected (see FIG. 1). The PDMS based microfluidic chip contains three individual chambers, interconnected by two micropillar arrays. While the two outer chambers form the medium channels, the middle chamber is designed to accommodate the differentiating hMO in a three-dimensional matrix. By adjusting the filling volumes on both sites of the microfluidic chip various hydrostatic pressures can be generated and subsequently direct medium flow of different velocities not only through the hydrogel matrix within the central channel, but also through the embedded organoid. Therefore, nutrient supply is not limited to diffusion, but nutrients are actively transported to the embedded organoid, while simultaneously keeping shear forces at a minimum.

CFD Simulation of Microfluidic Platform Reveals Interstitial Flow Behavior

To assess overall flow characteristics within the microfluidic device a computational fluid dynamic (CFD) simulation was performed. The simulation was specifically set out to address platform specific correlations of overall volume flow rates and average velocity magnitudes within the central hydrogel chamber as a function of the relative inlet pressure.

For this purpose, the hydrostatic pressure driven flow design was split in 136000 hexahedral control volumes, with an example grid depicted in FIG. 2A, indicating the inflow and outflow boundary zones in blue and red, respectively.

The flow within the microfluidic device was shown to behave strictly laminarly, consequently resulting in a linear relationship between inlet pressure and volume flow rate. Initial assessment further revealed that the pressure drop within the microfluidic device can be mainly attributed to the hydrogel chamber, with negligible pressure loss resulting from the geometry of the device itself (see FIG. 2B). As a result thereof, a proportionality function between flow rate and pressure drop was established, allowing for the calculation of flow velocity as a function of matrix permeability.

Overall, the volume flow within the hydrogel matrix of the microfluidic device was shown to behave highly uniformly throughout the most part of the chamber.

Figure 2:
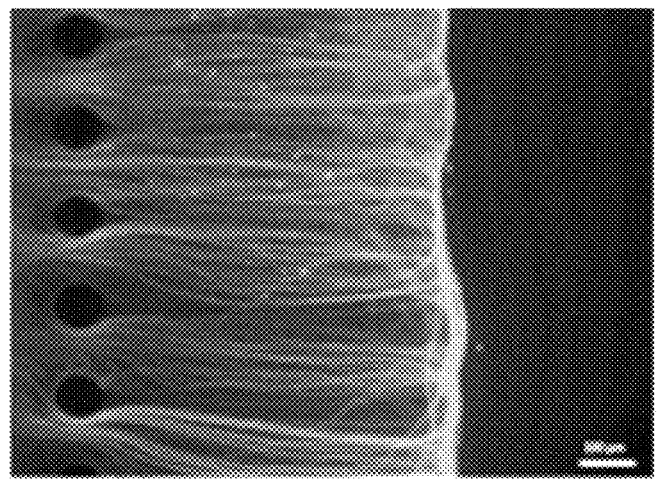
FIG. 2 shows a micrograph revealing flow alignment of calcein AM stained neurites.

Parallelly aligned streamlines retrieved from the simulation at a pressure difference of 1 mm confirm the aforementioned uniform velocity profile with an average velocity of 0.7 μm/s within the central part of the hydrogel chamber (see FIG. 2 C). While the comb structure of the micropillar array creates velocity gradients at the border of the hydrogel, the velocity within the hydrogel chamber behaves uniformly (see FIG. 2 D). Higher velocities within the border zone also alter the velocity profiles and thus may induce shear stress on the embedded organoid. Since the occurrence, however, is restricted to both the upper and lower part of the hydrogel chamber flow inflicted shear stress on the organoid situated within the middle of the chamber can be ruled out. Due to the uniform distribution of flow velocities within the central hydrogel chamber and thus absence of velocity gradients, shear stresses within the central part of the chamber are kept at a minimum and thus generate optimal culture conditions for hMOs.

Based on the CFD simulation an initial reservoir pressure difference of 2.4 mm was selected to drive interstitial fluid flow through the hydrogel and thus provide optimal culture conditions for the organoid.

By applying said hydrostatic pressure, hMOs are kept under dynamic culture conditions with flow velocities ranging from 1.6 μm/s (the upper limit of interstitial flow) down to 0.1 μm/s (the lower limit of interstitial flow) after 9 h of cultivation before the flow ultimately stops by hour 15. To prevent the undesired wash out of signaling molecules, a crucial parameter in cell-cell interactions and organoid maturation, reservoirs were refilled every 48 hours resulting in an alternating protocol of 15 h dynamic cultivation followed by a 33 h long static cultivation period.

Finally, to validate CFD simulation data, a FITC diffusion assay was employed. FITC data were shown to be in good agreement with the calculated fluid regime with an initial measured average velocity of 1.67±0.34 μm/s compared to an CFD estimated initial velocity of 1.6 μm/s.

Organoids Develop in Microfluidic Devices

After only four days of cultivation under said alternating cultivation protocol hMOs displayed extensive neurite outgrowth (see FIG. 3A), crucial for the formation of mature neural networks and the function of the nervous system[13]. While organoids cultivated on-chip for 24 h displayed an average neurite length of 293±78 μm (n=3 (30 neurites in total)), hMOs cultivated for 96 h already displayed processes extending throughout large sections of the hydrogel chamber with an average neurite length of 1024.4±193.3 μm, equivalent to an average growth rate of 274.5±26.1 μm/day.

To ensure hMO viability, organoids were analyzed using calcein AM/ethidium homodimer staining (see FIG. 3B). Overall, no impairment in organoid viability was detected over the entire cultivation period of 6 weeks with an average viability of 96.6±2.7% (see FIG. 3C). While organoid viability remained constant over the entire cultivation period, a significant increase in hMO size was detected. Whereas hMOs displayed an average diameter of 737.4±19.2 μm after one week of cultivation, the diameter increased up to 1082.6±66.2 μm after 6 weeks of culture within the microfluidic device (see FIG. 3C).

Intriguingly, hMOs cultivated within the microfluidic chip did not display pronounced dead cores, a key limitation in organoid technology. The diminution of necrotic cores characterized by a significant reduction in nuclear fragmentation visible upon staining with DAPI can be explained by coupling of active transport of nutrients with enhanced hMO outgrowth into the hydrogel matrix (see FIG. 3D).

To assess successful maturation of hMOs on-chip, D30 organoids were analyzed using immunohistochemistry for both tyrosine hydroxylase and TUJ1. Overall, hMOs cultivated on-chip displayed robust differentiation into TUJ1-positive neurons, a neuronal cell marker in the developing and mature human nervous system. Furthermore, hMOs stained positive for tyrosine hydroxylase an essential enzyme in the catecholamine synthesis pathway and marker for dopaminergic neurons, the main source of dopamine in the central nervous system and integral part of the human midbrain.

Notably, hMOs cultivated on-chip not only stained positive for TH, but in addition displayed neuromelanin granules. Neuromelanin are dark brown/black granular pigments that are situated within the substantia nigra of the human midbrain. When cultivated under physiologic conditions within our device the formation of neuromelanin granules was observed at day 30, an early stage of midbrain organoid development (see FIG. 3E). Histological analysis with Fontana Masson staining revealed the presence of both extra-cellular and intra-cellular neuromelanin, indicating that neuromelanin granules get secreted within the hMO (see FIG. 3F). In addition, preliminary studies using multi-electrode array (MEA) technology as well as calcium Fluo-4 staining revealed spontaneous electrophysiological activity after 30 days on-chip.

Chip Integrated Sensors Allow for Online Monitoring of Oxygen Consumption

To ensure proper oxygenation and to non-invasively monitor hMO viability and growth, luminescent based oxygen sensor spots were integrated into the microfluidic device (see FIG. 4A). While the partial oxygen pressure measured within the blank chips remained constant over the entire cultivation period of 6 weeks with an average of 190.7±16.7 hPa, thus ensuring sensor stability, a three-fold increase in oxygen demand could be detected in the chips carrying human midbrain organoids. Whereas a small increase in oxygen demand was measured during the first three initial weeks of cultivation ranging from 51.6±20.8 hpa up to 69.3±23.8 hPa a substantial increase could be detected by week 4 with an average oxygen demand of 92.5±17.3 hPa which further increased up to 144.4±17.1 hPa by week 6. Overall, the data indicates that hMOs cultivated within microfluidic chips not only remain viable for prolonged cultivation periods but actively grow under dynamic culture conditions further corroborating the data retrieved under the previous section.

DISCUSSION

In this example the production of a sensor-integrated microfluidic platform is shown, which addresses not only the three-dimensional cytoarchitecture of the human midbrain but in addition expands the model by the application of interstitial flow, a crucial parameter for nutrient transport, tissue maintenance as well as pathobiology. Overall, it was shown that hMOs could be cultivated for prolonged cultivation periods of up to 50 days, without the impairment of cellular viabilities, essential for long term studies required in the field of iPSC technology.

Microfluidic culture can be beneficial for neuronal differentiation while simultaneously provide an economically efficient route to personalized drug discovery for Parkinson disease. However, the microfluidic cultivation of individual neuroepithelial stem cells in a 3D matrix, has resulted in poor cellular viabilities associated with high stress exposure during cell loading, limiting its use within the tested set-up. While our milli-fluidic approach, has shown ameliorated differentiation behavior of hMOs combined with enhanced oxygen supply and a reduction in the necrotic core the throughput remained limited. By combining hMOs with microfluidic technology not only the aforementioned limitations such as low viabilities and throughput have been addressed but further improved aspects such as the diminution of necrotic cores and sensor integration enabling non-invasive monitoring.

Overall, our model integrates well with published midbrain-organoid literature. Similar to published microtiter plate set-ups hMOs cultivated within the presented microfluidic chip, not only stained positive for the neuronal cell marker TUJ1 as well as the dopaminergic neuron marker TH but also displayed spontaneous electrophysiological activity after 30 days of cultivation. A reduced expression of TH positive cells compared to our previous studies, can be explained by PDMS mediated absorption and adsorption of small molecules respectively, requiring adaptations in medium composition as well as surface treatments.

Remarkably, hMOs cultivated in microfluidic devices displayed visible neuromelanin granules as early as day 30, therefore significantly earlier when compared to other midbrain organoid literature where the onset of neuromelanin formation was reported between 45 and 100 days in culture. It has to be noted, that neuromelanin is concentrated in midbrain dopaminergic neurons of the substantia nigra, the brain region mostly affected by Parkinson's.

Neuromelanin is postnatal and restricted to humans and primates, therefore limiting its accessibility for neuromelanin related studies. While it is unclear whether neuromelanin formation was triggered by shear stress, the early onset of age-related phenomena seen within our microfluidic device underlines its potential use for addressing age-related questions, such as those relevant in Parkinson disease. Furthermore, the observed cellular alignment in the direction of the imposed flow, an important aspect in glia-mediated neuronal migration during neuronal development, might be a physiologic extension to the presented model and of great use for nervous system connection in future multi-organoid systems.

Overall, this example has provided a highly complex in vitro model that allows for non-invasive monitoring and is capable of emulating strong midbrain associated phenotypes in physiologic microenvironments that meet the need for relevant in vitro models and thus may provide a powerful tool in the context of Parkinson disease.

The invention claimed is:

1. A microfluidic device (1) for cultivating cells, comprising at least two fluid channels (2) positioned essentially opposite to each other and a main chamber (3) located between the fluid channels (2), wherein the main chamber (3) comprises at least one access opening, and each of the at least two fluid channels (2) is fluidly connected to the main chamber (3) at at least one point of contact (4), wherein a slotted structure (5) is provided at each point of contact (4) separating the main chamber (3) from the respective fluid channel (2), wherein the slotted structure (5) is permeable to a liquid, wherein the main chamber (3) comprises an inner top surface (6), an inner bottom surface (7) situated opposite to the inner top surface (6), and an array of pillars (8) extending from the inner top surface (6) into the cross section of the main chamber (3) in direction of the inner bottom surface (7), wherein the inner bottom surface (7) of the main chamber (3) comprises at least one recess (9).

2. The microfluidic device (1) according to claim 1, wherein the contact points (4) are formed by elongated contact areas located on opposite sides of the main chamber (3).

3. The microfluidic device (1) according to claim 2, wherein the distance between the elongated contact areas is smaller than a length of the main chamber (3) of the microfluidic device (1).

4. The microfluidic device (1) according to claim 1, wherein the at least one recess (9) has a substantial cylindrical or substantial hemispherical shape.

5. The microfluidic device (1) according to claim 1, wherein each of the at least two fluid channels (2) is fluidly connected to a respective fluid channel inlet (2*a*) and a respective fluid channel outlet (2*b*).

6. The microfluidic device (1) according to claim 5, wherein the fluid channel inlet (2*a*) and the fluid channel outlet (2*b*) are fluidly connected to medium reservoirs (2*c*, 2*d*, 2*e*, 2*f*).

7. The microfluidic device (1) according to claim 6, wherein the medium reservoirs (2*c*, 2*f*) fluidly connected to the fluid channel inlet (2*a*) have a larger volume than the medium reservoirs (2*d*, 2*e*) fluidly connected to the fluid channel outlet (2*b*).

8. The microfluidic device (1) according to claim 6, wherein the medium reservoirs (2*c*, 2*f*) fluidly connected to the fluid channel inlet (2*a*) have a smaller volume than the medium reservoirs (2*d*, 2*e*) fluidly connected to the fluid channel outlet (2*b*).

9. The microfluidic device (1) according to claim 6, wherein the medium reservoirs (2*c*, 2*f*) fluidly connected to one fluid channel (2) of the at least two fluid channels have a larger volume than the medium reservoirs (2*d*, 2*e*) fluidly connected to another fluid channel (2) of the at least two fluid channels.

10. The microfluidic device (1) according to claim 1, wherein the slotted structure (5) comprises an electrically conductive material to form an electrode.

11. The microfluidic device (1) according to claim 1, wherein the slots of the slotted structure (5) are spaced apart from each other by at least 50 μm.

12. The microfluidic device (1) according to claim 1, wherein an inner surface of the main chamber, an inner surface of the at least two fluid channels (2), and/or the slotted structure (5) is covered by an antifouling layer.

13. The microfluidic device (1) according to claim 1, wherein the array of pillars (8) extending from the inner top surface (6) into the cross section of the main chamber (3) in direction of the inner bottom surface (7) comprises at least some pillars connecting the inner top surface (6) and the inner bottom surface (7).

14. The microfluidic device (1) according to claim 1, wherein the access opening is sealable.

15. The microfluidic device (1) according to claim 11, wherein the slots of the slotted structure (5) are spaced apart from each other by at least 80 μm.

16. The microfluidic device (1) according to claim 11, wherein the slots of the slotted structure (5) are spaced apart from each other by at least 100 μm.

17. The microfluidic device (1) according to claim 11, wherein the slots of the slotted structure (5) are spaced apart from each other by at least 120 μm.

\*   \*   \*   \*   \*